United States Patent
Lee

(10) Patent No.: US 11,832,873 B2
(45) Date of Patent: Dec. 5, 2023

(54) CANNULAS FOR RADIO FREQUENCY ABLATION

(71) Applicant: Eric Lee, Camarillo, CA (US)

(72) Inventor: Eric Lee, Camarillo, CA (US)

( * ) Notice: Subject to any disclaimer, the term of this patent is extended or adjusted under 35 U.S.C. 154(b) by 315 days.

(21) Appl. No.: 16/896,340

(22) Filed: Jun. 9, 2020

(65) Prior Publication Data

US 2020/0390491 A1 Dec. 17, 2020

Related U.S. Application Data

(60) Provisional application No. 62/861,819, filed on Jun. 14, 2019.

(51) Int. Cl.
*A61B 18/14* (2006.01)
*A61B 18/00* (2006.01)

(52) U.S. Cl.
CPC ............... *A61B 18/1477* (2013.01); *A61B 2018/00083* (2013.01); *A61B 2018/00154* (2013.01); *A61B 2018/00577* (2013.01); *A61B 2018/1405* (2013.01)

(58) Field of Classification Search
CPC ........ A61B 18/1477; A61B 2018/1425; A61B 2018/1427; A61B 2018/00083; A61B 2018/00154; A61B 2018/00577; A61B 2018/1405; A61B 2018/1497; A61B 2218/002
See application file for complete search history.

(56) References Cited

U.S. PATENT DOCUMENTS

| | | | | |
|---|---|---|---|---|
| 5,458,597 A * | 10/1995 | Edwards | ............ | A61B 18/1482 606/49 |
| 5,792,140 A * | 8/1998 | Tu | ............ | A61B 18/08 606/41 |
| 5,919,188 A * | 7/1999 | Shearon | ............ | A61N 1/06 606/41 |
| 6,015,407 A * | 1/2000 | Rieb | ............ | A61N 1/056 606/41 |
| 6,514,261 B1 * | 2/2003 | Randall | ............ | A61F 2/95 604/528 |
| 6,712,812 B2 * | 3/2004 | Roschak | ............ | A61B 8/445 606/41 |

(Continued)

*Primary Examiner* — Michael F Peffley
(74) *Attorney, Agent, or Firm* — Lawrence B. Goodwin; Mandelbaum Barrett PC

(57) ABSTRACT

An ablation cannula comprising a tubular body, a tip at an end of the tubular body adapted to facilitate the insertion of the cannula into a vein or body cavity, the tip having a distal end, a transducer disposed within the tip, and at least one bore hole in the tip through which a medication or other fluid may be administered, wherein the borehole is separated from the distal end of the tip by a first distance, which may be approximately 2.5 millimeters. The tip may contain at least three boreholes substantially equally spaced around the circumference of the tip. The boreholes may have a diameter of approximately 0.21-0.51 millimeters. Additional configurations are described herein. The transducer is preferably a radio frequency transducer, and an insulative material may be disposed on a selected portion of the tip to attenuate energy emitted from the radio frequency transducer through the insulative material.

16 Claims, 2 Drawing Sheets

(56) References Cited

U.S. PATENT DOCUMENTS

| | | | | |
|---|---|---|---|---|
| 6,770,070 B1 * | 8/2004 | Balbierz | ........... | A61B 17/00491 |
| | | | | 606/41 |
| 7,311,708 B2 * | 12/2007 | McClurken | ........ | A61B 18/1492 |
| | | | | 606/50 |
| 8,128,620 B2 * | 3/2012 | Wang | ................. | A61B 18/1492 |
| | | | | 606/41 |
| 8,273,082 B2 * | 9/2012 | Wang | ................. | A61B 18/1492 |
| | | | | 606/41 |
| 8,535,306 B2 * | 9/2013 | Pearson | ............. | A61B 18/1482 |
| | | | | 606/49 |
| 8,702,697 B2 * | 4/2014 | Curley | ............... | A61B 18/1477 |
| | | | | 606/41 |
| 2006/0122593 A1 * | 6/2006 | Jun | ................... | A61B 18/1477 |
| | | | | 606/41 |
| 2009/0326439 A1 * | 12/2009 | Chomas | ............ | A61B 18/1477 |
| | | | | 604/21 |

* cited by examiner

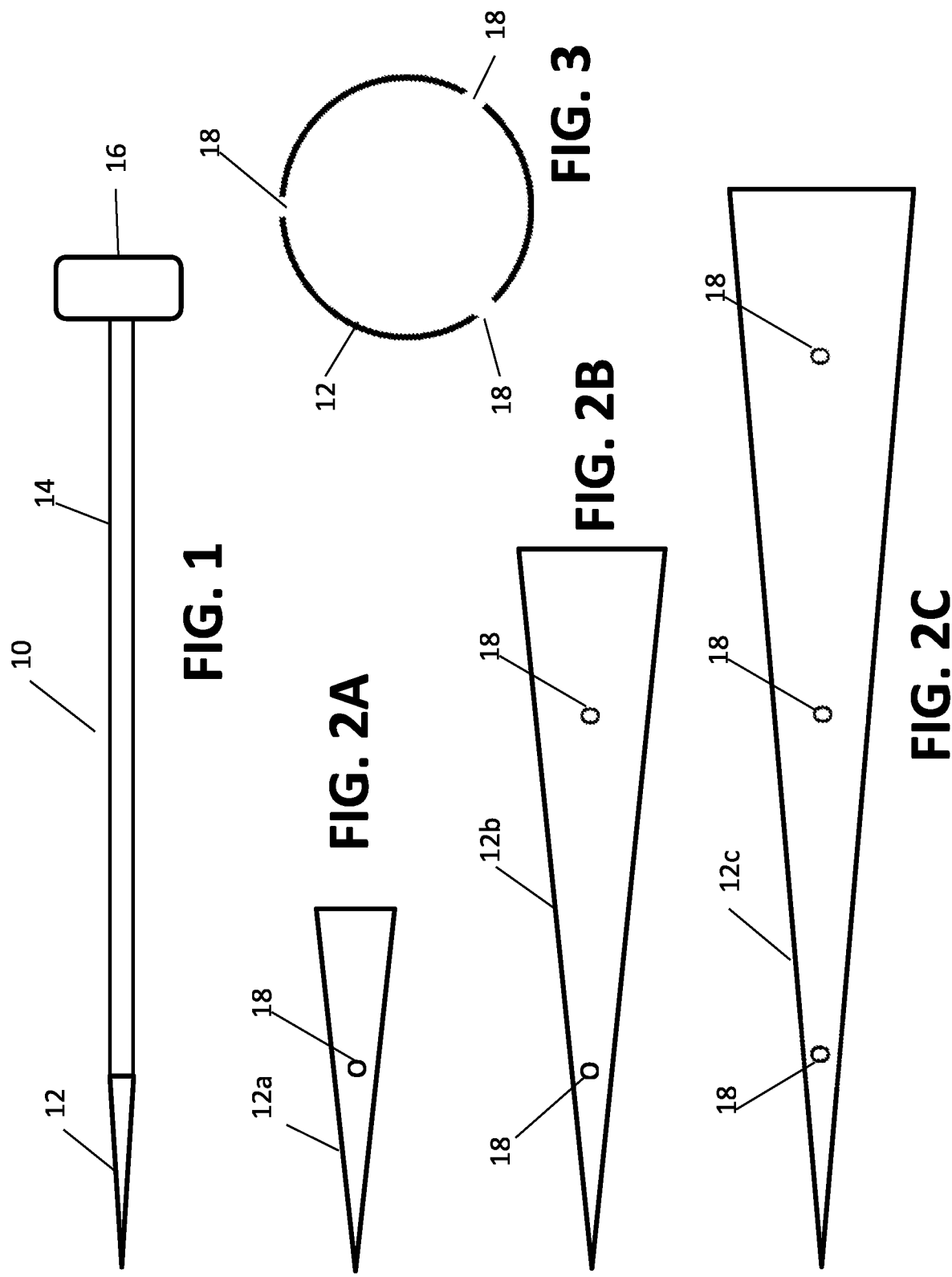

CANNULAS FOR RADIO FREQUENCY ABLATION

CROSS REFERENCE TO RELATED APPLICATION

This application claims the benefit of U.S. provisional application Ser. No. 62/861,819, filed Jun. 14, 2019, the entire disclosure of which is hereby incorporated by reference.

FIELD OF THE INVENTION

The present invention relates to the field of cannulas, and in particular, cannulas adapted for use in radio frequency ablation.

BACKGROUND

A cannula is a thin tube inserted into a vein or body cavity to administer medicine, drain a fluid, or insert a surgical instrument. The tip or end of a cannula is usually adapted to perform a specific task. For example, the tip of a cannula designed to administer a medication will have an opening at the tip from which the medication exits. Cannulas adapted for other functions, for example, ablation of lesions through the application of radio frequency (RF) energy, provide for the insertion of an RF transducer into the tip of the cannula to ablate a lesion at or near the tip. Such cannulas may be closed at the tip, or may have an opening at the tip to administer a steroid or anesthetic before or during an ablation procedure. It has been found, however, that such RF ablation cannulas have not been able to adequately administer medication, such as a steroid or anesthetic, since a subject nerve, for example, is usually located to the side of the cannula, not at the distal end of the tip. Another shortcoming of such RF ablation cannulas has been the inability to direct the RF energy toward a particular location, to cause ablation on one side of the cannula, but prevent ablation of tissue in other directions.

OBJECTS OF THE INVENTION

It is therefore an object of the invention to provide an ablation cannula that can overcome the foregoing difficulties, and in particular, provide an RF ablation cannula that can administer a medication more effectively than the prior art, and selectively apply RF energy to desired areas without applying such energy where it is not desired.

In accordance with one aspect of the invention, an ablation cannula comprises a tubular body, a tip at an end of the tubular body adapted to facilitate the insertion of the cannula into a vein or body cavity, the tip having a distal end, a transducer disposed within the tip, and at least one bore hole in the tip through which a medication or other fluid may be administered, wherein the at least one borehole is separated from the distal end of the tip by a first distance. The first distance may be approximately 2.5 millimeters. The tip may contain at least three boreholes substantially equally spaced around the circumference of the tip. The boreholes may have a diameter of approximately 0.21-0.51 millimeters. Additional configurations are described herein. The transducer is preferably a radio frequency transducer, and an insulative material may be disposed on a selected portion of the tip to attenuate energy emitted from the radio frequency transducer through the insulative material. Preferably, the insulative material may be comprised of silicon.

In accordance with another aspect of the invention, an ablation cannula comprises a tubular body, a tip at an end of the tubular body adapted to facilitate the insertion of the cannula into a vein or body cavity, a transducer disposed within the tip, and an insulative material disposed on a selected portion of the tip to attenuate energy emitted from the transducer through the insulative material. The transducer is preferably a radio frequency transducer and the insulative material is preferably comprised of silicon. The cannula may also include at least one bore hole in the tip through which a medication or other fluid may be administered, and preferably, the at least one borehole is separated from the distal end of the tip.

BRIEF DESCRIPTION OF THE DRAWINGS

These and other objects and aspects of the present invention will be described with reference to the following drawing figures, of which:

FIG. 1 is an illustration of an ablation cannula;

FIGS. 2A-2C illustrate cannula tips in accordance with one aspect of the present invention;

FIG. 3 is an axial cross-sectional view of the cannula tips of FIGS. 2A-2C.

DETAILED DESCRIPTION OF THE INVENTION

Figure 4B:
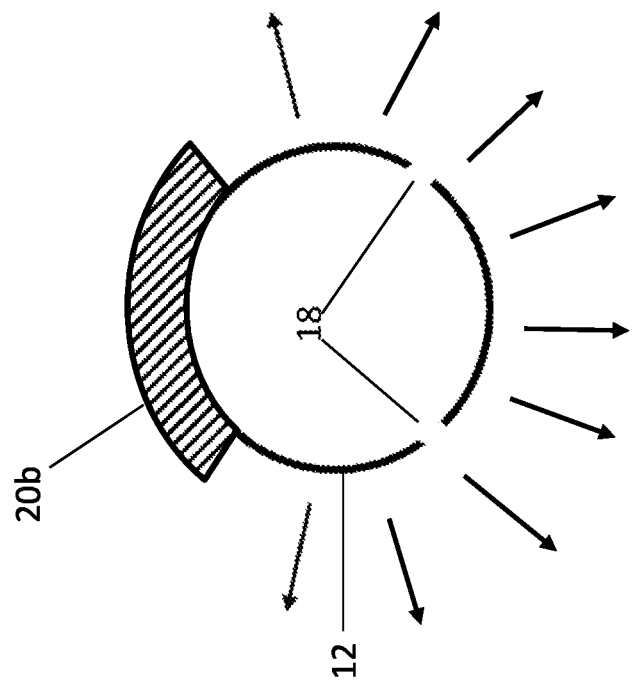
FIGS. 4A-4B illustrate cannula tips in accordance with another aspect of the present invention.

As shown in FIG. 1, an ablation cannula 10 is adapted to be inserted into a blood vessel or body cavity of a patient to ablate a lesion. The cannula is comprised of a tip 12 and a tubular body 14, usually made of stainless steel or a nickel-titanium alloy. A power source and controls 16 are also provided for an RF transducer, which is inserted into the cannula and disposed within the tip 12. Typically, the cannula will be of 16, 18, 20 or 22 gauge, and can be straight or curved, but other configurations will be apparent to those skilled in the art, in view of the present description.

In accordance with one aspect of the present invention, three examples of active tips 12 are shown in FIGS. 2A-2C. In FIG. 2A, a cannula tip 12a has a length of approximately 5 mm and is provided with three bore holes 18 (only one of which is shown in FIG. 2A) located approximately 2.5 mm from the tip, through which a medication can be dispensed. FIG. 3 is an axial cross-sectional view of the cannula tip 12 and illustrates the positions of the three boreholes 18 which are equally spaced around the periphery of the tip at approximately 12 o'clock, 4 o'clock and 8 o'clock positions. The boreholes preferably have a diameter of approximately 0.21 mm-0.51 mm, although other sizes can be used as well. FIG. 2B illustrates a cannula tip 12b that has a length of approximately 10 mm and is provided with three bore holes 18 located approximately 2.5 mm from the tip and another three boreholes located approximately at 7.5 mm from the tip. The boreholes are equally spaced around the periphery of the tip, as explained with reference to FIG. 3. Finally, FIG. 2C illustrates a cannula tip 12c that has a length of approximately 15 mm and is provided with three bore holes 18 located approximately 2.5 mm from the tip, another three boreholes located approximately at 7.5 mm from the tip, and another three boreholes located approximately at 12.5 mm from the tip. Again, the boreholes are equally spaced around the periphery of the tip, as explained with reference to FIG. 3.

Except for the bore holes 18, as described above, the cannula tip 12 is closed. This configuration facilitates the application of a medication precisely to the desired location relative to the lesion.

Figure 4A:
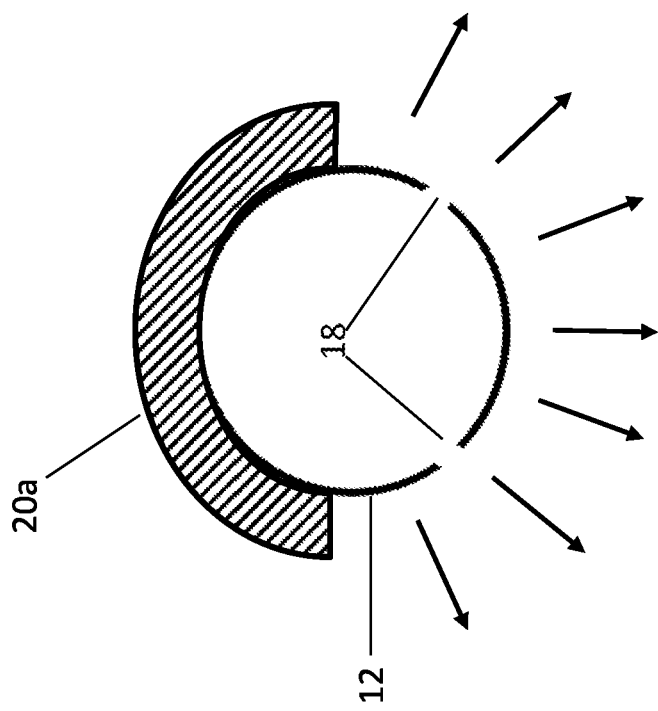

In accordance with another aspect of the present invention, insulation effective to prevent RF energy from propagating therethrough is provided around selected portions of the tip, to directionally ablate—or not—in a particular direction, as desired. In FIG. 4A, insulation 20*a* is provided around approximately 180° about the periphery of the tip 12, such that the RF energy is applied in the direction of the arrows, but not elsewhere. Similarly, In FIG. 4B, insulation 20*b* is provided around approximately 90° about the periphery of the tip 12, such that the RF energy is applied in the direction of the arrows, but not elsewhere. In accordance with a preferred embodiment, the insulation can be formed of silicon, although other materials may be used if desired.

Accordingly, the cannula in accordance with this aspect of the invention may provide selective ablation of a lesion without ablating surrounding tissue. In the event boreholes 18 are employed along with the insulation, only two boreholes may be used, although the third borehole may be provided through the insulation if desired.

Further objects, aspects and embodiments of the present invention will be appreciated by those skilled in the art, in view of the foregoing. While the foregoing is directed to embodiments of the present invention, other and further embodiments of the invention may be devised without departing from the basic scope thereof, as defined by the following claims.

I claim:

1. An ablation cannula comprising:
   a. a tubular body and a tapered section forming a tip at an end of said tubular body, said tapered section being tapered to form a pointed distal end, said tubular body and said tapered section having a fluid path through which a medication or other fluid may be administered;
   b. wherein (i) said tapered section has a surface consisting essentially of metal, (ii) said pointed distal end facilitates the insertion of said cannula into a patient to ablate a lesion, and (iii) said pointed distal end is closed to thereby prevent said medication or fluid from exiting said cannula from said pointed distal end;
   c. a transducer disposed within said tip; and
   d. a plurality of bore holes in communication with said fluid path and located in, and only in, said tapered section through which said medication or other fluid may be administered, wherein said at least one borehole is separated from said distal end of said tip by a first distance, and wherein said medication or other fluid can be administered, and only administered, from said tapered section at a location separated from said distal end of said tip.

2. The ablation cannula of claim 1 wherein said first distance is approximately 2.5 millimeters.

3. The ablation cannula of claim 1 wherein said tip contains at least three boreholes substantially equally spaced around the circumference of said tip.

4. The ablation cannula of claim 3 wherein said boreholes have a diameter of approximately 0.21-0.51 millimeters, and said first distance is approximately 2.5 millimeters.

5. The ablation cannula of claim 4 wherein said tip is approximately 5 millimeters in length.

6. The ablation cannula of claim 4 further comprising three boreholes located approximately 7.5 millimeters from said distal end of said tip and substantially equally spaced around the circumference of said tip.

7. The ablation cannula of claim 6 wherein said tip is approximately 10 millimeters in length.

8. The ablation cannula of claim 6 further comprising three boreholes located approximately 12.5 millimeters from said distal end of said tip and substantially equally spaced around the circumference of said tip.

9. The ablation cannula of claim 8 wherein said tip is approximately 15 millimeters in length.

10. The ablation cannula of claim 1 wherein at least first and second sets of boreholes are provided in said tip, each of said sets comprised of a plurality of boreholes substantially equally spaced around the circumference of said tip, said first set located at a first distance from said distal end, and said second set located at a second distance from said distal end, wherein said second distance is greater than said first distance.

11. The ablation cannula of claim 10 further comprising a third set of a plurality of boreholes substantially equally spaced around the circumference of said tip and located at a third distance from said distal end, wherein said third distance is greater than said second distance.

12. The ablation cannula of claim 1 wherein said transducer is a radio frequency transducer.

13. The ablation cannula of claim 12 further comprising an insulative material continuously, circumferentially, and only disposed on a selected portion of said tip, said selected portion being less than the full circumference of said tip, to attenuate energy emitted from said radio frequency transducer through said insulative material to thereby direct said energy in a direction away from said selected portion.

14. The ablation cannula of claim 13 wherein said insulative material is comprised of silicon.

15. The ablation cannula of claim 13 wherein said selected portion is along approximately 180 degrees of said tip.

16. The ablation cannula of claim 13 wherein said selected portion is along approximately 90 degrees of said tip.

* * * * *